United States Patent
Granegger et al.

(10) Patent No.: US 12,109,404 B2
(45) Date of Patent: Oct. 8, 2024

(54) BLOOD PUMP FOR MECHANICAL CIRCULATORY SUPPORT FOR FONTAN PATIENTS

(71) Applicant: UNIVERSITÄT ZÜRICH, Zürich (CH)

(72) Inventors: Marcus Granegger, Zürich (CH); Michael Hübler, Herrliberg (CH); Bente Thamsen, Zürich (CH); Martin Schweiger, Stallikon (CH)

(73) Assignee: UNIVERSITÄT ZÜRICH, Zurich (CH)

(*) Notice: Subject to any disclaimer, the term of this patent is extended or adjusted under 35 U.S.C. 154(b) by 810 days.

(21) Appl. No.: 16/973,832

(22) PCT Filed: Jun. 11, 2019

(86) PCT No.: PCT/EP2019/065211
§ 371 (c)(1),
(2) Date: Dec. 10, 2020

(87) PCT Pub. No.: WO2019/238677
PCT Pub. Date: Dec. 19, 2019

(65) Prior Publication Data
US 2021/0268262 A1 Sep. 2, 2021

(30) Foreign Application Priority Data
Jun. 11, 2018 (EP) .................................... 18176928

(51) Int. Cl.
*A61M 60/00* (2021.01)
*A61M 60/148* (2021.01)
(Continued)

(52) U.S. Cl.
CPC ........ *A61M 60/515* (2021.01); *A61M 60/148* (2021.01); *A61M 60/226* (2021.01);
(Continued)

(58) Field of Classification Search
CPC .............. A61M 60/515; A61M 60/226; A61M 60/422; A61M 60/82; A61M 2205/04; A61M 2205/3334; A61M 2250/00
See application file for complete search history.

(56) References Cited

U.S. PATENT DOCUMENTS 5,840,070 A * 11/1998 Wampler ................. H02K 7/09
417/423.1
6,074,180 A * 6/2000 Khanwilkar ........ A61M 60/232
417/420
(Continued)

FOREIGN PATENT DOCUMENTS

CN 1222862 7/1999
CN 101361994 2/2009
(Continued)

*Primary Examiner* — Eric D. Bertram
(74) *Attorney, Agent, or Firm* — JMB Davis Ben-David

(57) ABSTRACT

The invention relates to a radial blood pump (1) for supporting a blood flow (106) in a human or animal heart (205) comprising a first and a second inlet channel (41, 42), a first outlet channel (51, 52), a first electric motor (71) comprising a first stator (77) and a first internal rotor (75), wherein the first electric motor (71) is configured to drive an impeller (2, 2a, 2b) arranged at an intersection of the first with the second inlet channel (41, 42), wherein the impeller (2, 2a, 2b) is connected to the first internal rotor (75) and wherein the impeller (2, 2a, 2b) comprises a merging portion (22) arranged at the intersection, where a merging of a first blood flow (106) coming from the first inlet channel (41) and a second blood flow (107) coming from the second inlet channel (42) takes place, wherein the impeller (2, 2a, 2b) is configured to pump the first and second blood flow (106, 107) from the first and second inlet channel (41, 42) via the merging portion (22) to the first outlet channel (51), a plurality of blades (20) comprised by the impeller (2, 2a, 2b), wherein the blades (20) form blade channels (21)
(Continued)

Figure 1:
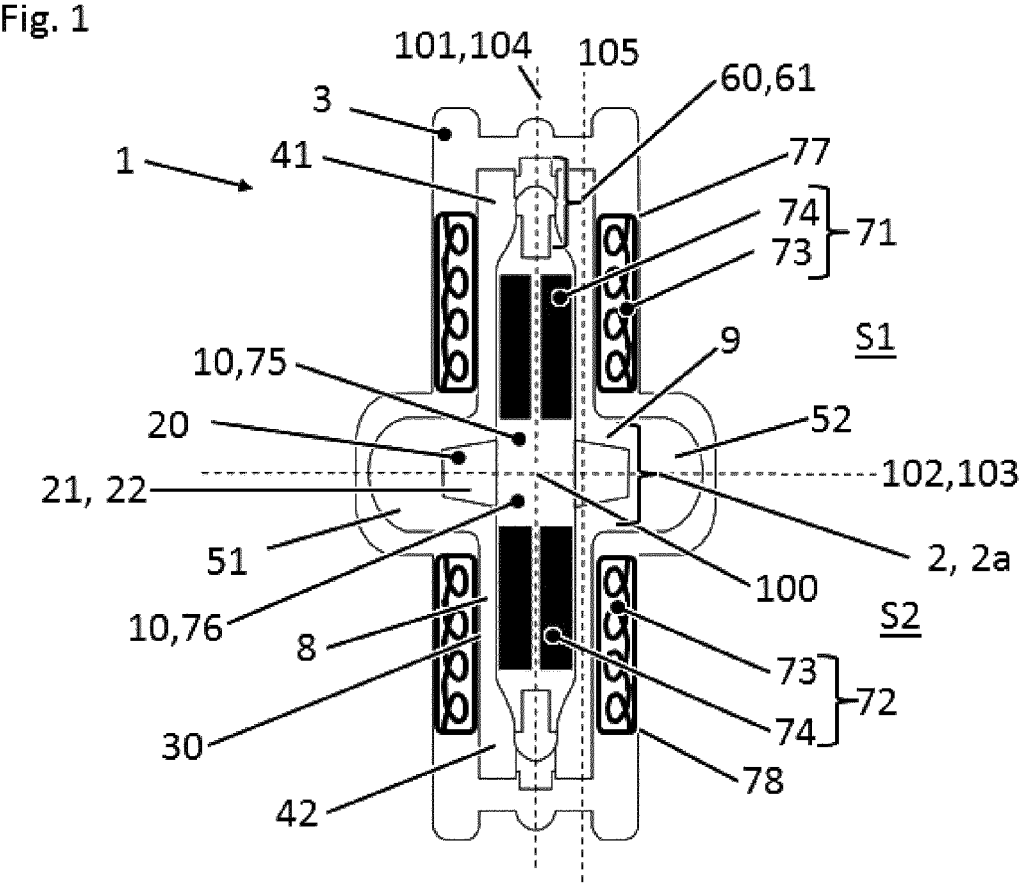

comprised by the merging portion (22), wherein each blade (20) is arranged and configured to pump the first and second blood (106, 107) flow entering through the first and the second inlet channel (41, 42) towards the outlet channel (51), wherein the blood pump (1) is arranged and configured such that the first blood flow (106) and the second blood flow (107) meet at the merging portion (22), such that a pressure difference between the first and second blood flow (106, 107) is reduced before blood from first and second blood flow (106, 107) is pumped to the first outlet channel (51).

16 Claims, 6 Drawing Sheets

(51) Int. Cl.

| | | |
|---|---|---|
| *A61M 60/226* | (2021.01) | |
| *A61M 60/35* | (2021.01) | |
| *A61M 60/422* | (2021.01) | |
| *A61M 60/515* | (2021.01) | |
| *A61M 60/531* | (2021.01) | |
| *A61M 60/538* | (2021.01) | |
| *A61M 60/806* | (2021.01) | |
| *A61M 60/81* | (2021.01) | |
| *A61M 60/82* | (2021.01) | |
| *A61M 60/825* | (2021.01) | |

(52) U.S. Cl.
CPC .......... *A61M 60/35* (2021.01); *A61M 60/422* (2021.01); *A61M 60/531* (2021.01); *A61M 60/538* (2021.01); *A61M 60/806* (2021.01); *A61M 60/81* (2021.01); *A61M 60/82* (2021.01); *A61M 60/825* (2021.01); *A61M 2205/04* (2013.01); *A61M 2205/3334* (2013.01); *A61M 2250/00* (2013.01)

(56) References Cited

U.S. PATENT DOCUMENTS

| | | | | | |
|---|---|---|---|---|---|
| 6,149,683 | A * | 11/2000 | Lancisi | ............... | A61M 60/585 |
| | | | | | 600/16 |
| 6,155,969 | A * | 12/2000 | Schima | ................ | A61M 60/113 |
| | | | | | 600/16 |
| 6,234,998 | B1 * | 5/2001 | Wampler | ............. | H02K 5/1285 |
| | | | | | 604/131 |
| 6,302,661 | B1 * | 10/2001 | Khanwilkar | ........ | A61M 60/422 |
| | | | | | 417/423.12 |
| 6,368,083 | B1 * | 4/2002 | Wampler | ............ | A61M 60/422 |
| | | | | | 417/423.1 |
| 6,527,699 | B1 * | 3/2003 | Goldowsky | ......... | A61M 60/825 |
| | | | | | 600/16 |
| 6,595,762 | B2 * | 7/2003 | Khanwilkar | ........ | F04D 13/0666 |
| | | | | | 417/420 |
| 6,688,861 | B2 * | 2/2004 | Wampler | ............ | A61M 60/232 |
| | | | | | 417/423.1 |
| 8,777,832 | B1 * | 7/2014 | Wang | ................... | A61M 60/806 |
| | | | | | 600/16 |
| 9,901,666 | B2 * | 2/2018 | Cotter | ................. | A61M 60/232 |
| 2003/0176760 | A1 * | 9/2003 | El Oakley | ........... | A61M 60/148 |
| | | | | | 600/16 |
| 2004/0064012 | A1 * | 4/2004 | Yanai | ................... | A61M 60/546 |
| | | | | | 600/16 |
| 2004/0143151 | A1 * | 7/2004 | Mori | ................... | A61M 60/109 |
| | | | | | 600/16 |
| 2005/0107657 | A1 * | 5/2005 | Carrier | ...................... | F04D 3/02 |
| | | | | | 600/16 |
| 2007/0100196 | A1 * | 5/2007 | LaRose | ................. | A61M 60/81 |
| | | | | | 600/16 |
| 2010/0174131 | A1 * | 7/2010 | Foster | ................. | A61M 60/824 |
| | | | | | 600/16 |
| 2011/0237863 | A1 * | 9/2011 | Ricci | .................... | A61M 60/422 |
| | | | | | 29/598 |
| 2011/0257462 | A1 * | 10/2011 | Rodefeld | ............ | A61M 60/216 |
| | | | | | 600/16 |
| 2012/0004497 | A1 * | 1/2012 | Ayre | .................... | A61M 60/232 |
| | | | | | 600/17 |
| 2012/0078030 | A1 * | 3/2012 | Bourque | ............ | A61M 60/546 |
| | | | | | 600/16 |
| 2012/0095280 | A1 * | 4/2012 | Timms | ................ | F04D 13/0633 |
| | | | | | 600/16 |
| 2012/0245680 | A1 * | 9/2012 | Masuzawa | .......... | A61M 60/538 |
| | | | | | 623/3.11 |
| 2014/0336446 | A1 * | 11/2014 | Rodefeld | ............ | A61M 60/148 |
| | | | | | 600/16 |
| 2015/0246166 | A1 * | 9/2015 | Greatrex | ............. | A61M 60/178 |
| | | | | | 600/17 |
| 2017/0239407 | A1 * | 8/2017 | Hayward | ............ | A61M 60/148 |
| 2019/0001037 | A1 * | 1/2019 | Bonde | ................. | A61M 60/216 |

FOREIGN PATENT DOCUMENTS

| | | |
|---|---|---|
| CN | 105214153 | 1/2016 |
| CN | 105307700 | 2/2016 |
| CN | 205792106 | 12/2016 |
| CN | 107080870 | 8/2017 |
| CN | 108025122 | 5/2018 |
| CN | 108136191 | 6/2018 |
| JP | 2014528771 | 10/2014 |
| WO | 2005020848 | 3/2005 |
| WO | 2013025826 | 2/2013 |
| WO | 2017021846 | 2/2017 |

* cited by examiner

BLOOD PUMP FOR MECHANICAL CIRCULATORY SUPPORT FOR FONTAN PATIENTS

CROSS-REFERENCE TO RELATED APPLICATIONS

This is the U.S. National Stage of International Patent Application No. PCT/EP2019/065211 filed on Jun. 11, 2019, which in turn claims the benefit of European Patent Application No. 18176928.2 filed on Jun. 11, 2018.

Specification

The invention relates to a blood pump for a human or animal heart, particularly to a pump which assists the Fontan circulation in cavopulmonary position, and a system comprising the blood pump.

The invention further relates to a method for adjusting the blood pump rate according to a measured or estimated hemodynamic signal.

In the USA and Europe, approx. 1% of all live births are children born with a congenital heart defect. Approx. 5 to 10% of these patients suffer from an underdeveloped left or right ventricle: consequently, their circulatory system comprises only one functional ventricle. Because arterial oxygen saturation in this configuration is low and the single ventricle is permanently overloaded, a lack of treatment will inevitably lead to the death of the patient.

The only two treatment options are either heart transplantation or the creation of the so-called "Fontan circulation" [1], [2]. Whereas the availability of donor organs is limited especially for children, the second option offers a palliative perspective with reported survival rates ranging from less than 50% to 76% for thirty years [3], [4].

Therefore, mechanical circulatory support (MCS) devices constitute the most promising approach to enhance cardiovascular system function in Fontan patients. Some MCS devices specifically designed for cavopulmonary support have been proposed for the Fontan circulation in the literature [5]-[7].

Other clinically available approaches are left ventricular assist devices (LVADs) or right ventricular assist devices (RVADs) with the aim to bridge the time span of the patient to transplantation.

None of these constitutes an option for long-term therapy in Fontan patients owing to their design, size and/or their invasivity.

An object of the present invention is to provide an MCS device for enhancing the cardiovascular system function in Fontan patients. The object is achieved by a radial blood pump having the features of claim 1.

Advantageous embodiments are described in the subclaims.

According to claim 1 the radial blood pump, particularly a cavopulmonary assist device, for supporting the blood circulation in a patient's heart comprises at least the following components:

A first and a second inlet channel that are particularly arranged opposite of each other, A first outlet channel, A first electric motor comprising a first stator particularly arranged at a pump housing and a first internal rotor, wherein the first electric motor is configured to drive an impeller, wherein The impeller is arranged at an intersection of the first inlet channel with the second inlet channel, wherein the impeller is connected to the first internal rotor, wherein the impeller comprises a particularly open merging portion arranged at the intersection, where a merging of a first particularly venous blood flow coming from the first inlet channel and a second particularly venous blood flow coming from the second inlet channel takes place, wherein the impeller is configured to pump the first and second blood flow from the first and second inlet channel via the merging portion particularly towards a volute chamber or a ring chamber that is connected to the first outlet channel, wherein the outlet channel is particularly arranged in a tangential direction with respect to the axis of rotation of the impeller, A plurality of blades comprised by the impeller, wherein the blades form blade channels comprising at least a part of the merging portion, wherein the blade channels are arranged between a pressure face of a blade and a suction face of a blade, wherein each blade is arranged and configured to pump the first and second blood flow entering through the first inlet channel and the second inlet channel towards the outlet channel, wherein the radial blood pump is arranged and configured such that the first blood flow and the second blood flow unite at the merging portion, particularly such that a pressure difference between the first and second blood flow is reduced or equalized particularly at the merging portion, before the blood of the first and second blood flow is pumped into the first outlet channel.

The radial pump is particularly designed and configured to assist the Fontan circulation in cavopulmonary position of a patient.

The merging portion particularly extends symmetrically around a central point of the radial blood pump.

Due to the radial design of the pump, the pump can be connected to the superior vena cava (SVC) and the inferior vena cava (IVC) with the first and the second inlet channel, while the first outlet channel can be connected to the pulmonary trunk or the left and/or the right pulmonary artery. The radial design of the pump particularly coincides with the anatomy of the venae and arteries in the total cavopulmonary connection of Fontan patients.

In the healthy physiologic condition, the IVC and SVC discharge against the right atrium and consequently against the same pressure. The right atrial pressure is an important determinant of venous return. Equalizing the pump inlet pressures in the IVC and SVC even in case of highly imbalanced blood flows may be of crucial importance to ensure physiologic perfusion of the upper and lower body. As the blood flow at the IVC is often somewhat larger than the blood flow from the SVC especially during physical activity, it is an important feature of the blood pump that a pressure difference between the SVC and the IVC is reduced or equalized in a merging portion of the impeller, particularly before the blood is pumped towards the outlet channel.

Particularly, the radial blood pump is configured to receive the first blood flow, particularly the IVC through the first inlet channel and the second blood flow, particularly the SVC through the second inlet channel, wherein the first blood flow has a larger pressure than the second blood flow, or vice versa, such that a pressure equalization between the two blood flows takes place at the merging portion of the pump. Particularly the pump is configured such that the first and the second blood flow particularly first merge at the merging portion of the blood pump, wherein at the merging portion any pressure difference between the first and the second blood flow is reduced or equalized and particularly wherein after the blood flows have merged the blood is pumped through the outlet first channel.

Moreover, as the blood flows unite prior to or simultaneously with the blood being pumped towards the outlet channel(s), particularly all blade channels of the impeller carry the combined blood flow of the first and second inlet channel, i.e. the pump is particularly devoid of distinct blades that are specifically configured and arranged on the impeller for pumping either the blood flow of the first or the second inlet channel.

The latter configuration that provides distinct blades for pumping blood either from the first inlet channel or second inlet channel has the drawback that pressure differences are largely maintained and depending on the pump speed either an overpressure in the IVC or a low pressure in the SVC is evoked.

An additional advantage of this design is that asymmetric forces acting on the impeller due to a possible blood pressure difference are reduced to a great extent. A design with two outlet channels particularly with two volute tongues reduces the radial forces, a symmetric inlet design with two inlet channels reduces the axial thrust.

Furthermore, the pump is configured as an inrunner—as opposed to an outrunner. An outrunner pump has its rotor driven by forces generated by magnets or coils that are arranged on components of the pump that are enclosed by the rotor. Inrunner pumps provide the driving force by magnets or coils that are arranged around the rotor, typically on the housing of the rotor. The pump according to the invention is an inrunner pump, which is reflected by the term "internal rotor".

An outrunner pump generally allows for a more compact design, however, the efficiency of an outrunner pump is generally lower and thus, the outrunner pump generates more heat that is dissipated to the blood pumped by the pump. As a result, the temperature of the pumped blood rises due to the heat dissipation of the pump, and the likelihood of a thrombus (also referred to as clot) formation increases dramatically.

A particular challenge for pumps in cavopulmonary location originates from floating thrombi coming from the venous system that have to be tolerated by the pump. From the recent clinical experience with the HeartMate III [8] it can be derived that large flow channels and a small number of leading edges may prevent pump thrombosis possibly by allowing for thrombi to pass through the pump instead of being trapped inside the device. Pumps with small gaps such as with hydrodynamic bearings, and structures as washout holes may be disadvantageous in this regard. The proposed motor and pump design facilitates the use of large gaps.

Configuring the pump according to the invention as an inrunner pump therefore reduces the risk of clot formation and thus also of pump clogging due to clots.

The first stator is particularly arranged at a pump housing encasing the first internal rotor. The first electric motor particularly comprises coils and permanent magnets.

According to an embodiment of the invention, the magnets are particularly arranged on the first rotor and the coils are arranged around the first internal rotor on the first stator.

The impeller is connected to the first internal rotor by means of a rigid connection, wherein the connection can be given for example by an integrally formed component that comprises the impeller and the first internal rotor. However, it is also possible that the impeller is connected by a connection means to the rotor, essentially forming a two-part device, having a rotor and an impeller connected to the rotor.

Where the first and the second inlet channel meet, an intersection is formed. Also, the first outlet channel is arranged at that intersection. The first outlet channel particularly extends radially with respect to an axis of rotation of the impeller.

In order to provide pressure equalization, the radial blood pump comprises the merging portion. The merging portion is configured such that the first particularly venous blood flow coming from the first inlet channel and a second particularly venous blood flow coming from the second inlet channel unite and particularly unite, particularly prior to or simultaneously with the blood being pumped by the blades of the pump towards the first outlet channel.

Depending on the specific design of the impeller, the blades can have various shapes and contours.

According to another embodiment of the invention, the blades are arranged in a single plane, wherein said plane is symmetrically arranged between the first and second channel.

This embodiment allows for pumping blood from the first and second inlet channel.

The blades particularly have a pressure face and a suction face that experience different pressure conditions during pumping.

The pressure face "pushes" the blood, whereas the suction face is a side of the blade that is particularly oriented counter to the pressure face. A pump effect takes places due to acceleration of the blood by the impeller.

Depending on the specific design of the impeller, particularly whether it is an open or a closed impeller, the merging portion particularly consists of the blade channels. This is particularly the case when the impeller is an open impeller.

In case the impeller is a closed impeller, or semi-closed impeller, the merging portion can further comprise the eye of the impeller. In blade channels and/or in the eye of the impeller blood flows unite and particularly mix prior to or simultaneous with the pumping of the blood towards the outlet channel.

According to another embodiment of the invention, the radial blood pump is configured for supporting a Fontan circulation at the cavopulmonary junction of a patient.

According to another embodiment of the invention, the radial blood pump comprises a second electric motor comprising a second stator and a second internal rotor that is rigidly connected to the first internal rotor.

The second motor provides redundancy in terms of motor failure of the first motor. Even with the first electric motor being incapacitated, the second electric motor is capable to maintain pumping of the blood, so that a critical situation for the patient is avoided.

Moreover, the second electric motor can be arranged at a different installation position of the pump and thus, the dissipated heat from the blood pump is distributed elsewhere within the blood pump, reducing the risk of a critical temperature rise of the pumped blood with respect to blood trauma and clot formation.

The first and the second motor are particularly arranged shifted along the axis of rotation of the impeller, wherein the first electric motor is particularly arranged closer to the first inlet channel than the second motor and the second electric motor is particularly arranged closer to the second inlet channel than the first motor.

Furthermore, the first and the second motor are particularly designed and arranged symmetrically with respect to the axis of rotation of the impeller such that resulting magnetic forces can be reduced or ideally balanced.

The second internal rotor is particularly integrally formed with the first internal rotor.

The second stator is particularly integrally formed with the first stator.

It is noted that both motors are particularly rigidly connected to each other, for example by means of a pump housing and a shaft, and wherein particularly both motors drive the same blades of the impeller.

Each motor however comprises its own set of coils and magnets that provide the driving force.

The second electric motor can be designed identical to the first electric motor, particularly wherein the second rotor can be integrally formed to the impeller, or be essentially a two-part device with a rotor and an impeller connected to each other by a connection means.

According to another embodiment of the invention, the first electric motor is arranged in a first half space extending from a plane extending orthogonally from an axis of rotation of the impeller comprising the first inlet channel and wherein the second electric motor is arranged in a particularly complementary second half space extending from the said plane comprising the second inlet channel.

This embodiment allows an even better heat distribution and facilitates a symmetric pump design allowing for symmetric forces.

This embodiment reduces wear and tear and allows for reduced energy consumption due to symmetric load distribution.

Moreover, this embodiment reduces design constraints on the stator topology of the pump, as particularly the coils can be arranged along the inlet channels, which leads to a space-efficient design.

According to this embodiment the rotors and stators of the first and second motor are arranged in corresponding half spaces, particularly on two sides of the impeller, e.g. above and below the impeller.

According to another embodiment of the invention, the impeller is a double suction impeller, particularly without a separating midplane, wherein the impeller is particularly a symmetric double suction impeller.

A double suction impeller allows for the provision of two opposing inlet channels. The double suction impeller allows distributing forces on the impeller symmetrically, reducing forces particularly on a magnetic bearing or reducing wear and tear particularly on mechanical bearings.

A double-suction impeller is configured to receive a blood flow from two sides of an impeller midplane, particularly from the two inlet channels.

According to another embodiment of the invention, the impeller is a closed double suction impeller, wherein the impeller comprises a first and a second shroud at least partially covering the blades and particularly the blade channels, and wherein the merging portion comprises two opposite eyes, particularly wherein each of the two eyes has a diameter that is larger than 2.5 mm, and more particularly larger than 7 mm.

According to this embodiment the merging portion comprises the eyes and/or the blade channels of the impeller, such that particularly efficient merging and particularly mixing of the blood flows from the first and second inlet channel is achieved prior to or simultaneous with pumping the blood flows from the first and second inlet channel towards the outlet channels.

Impeller eyes that have a diameter larger than 2.5 mm and more particularly larger than 7 mm avoid pressure losses before the two inlet flows meet and avoid clogging of the pump due to clots.

According to another embodiment of the invention, the first internal rotor of the first electric motor is arranged on the first shroud and particularly wherein the second internal rotor of the second electric motor is arranged on the second shroud.

This embodiment allows for a better heat dissipation, even if the two inlet flows are strongly imbalanced, while the symmetric layout reduces wear and tear on the pump.

Temperature generation in the motor and bearings affects hemocompatibility of a blood pump. Due to the small pressure head in the main operating condition compared to conventional blood pumps, the cooling of the motor region is challenging. Large fluid gaps to facilitate sufficient secondary flows are inevitable. In the proposed pumped, the dual motor configuration allows fluid gaps larger than 0.5 mm at acceptable temperature increase even at higher flow.

According to a variant of the invention, the impeller is an open particularly double suction impeller without shrouds, wherein the blades protrude from a shaft that extends along the axis of rotation of the impeller, wherein the first internal rotor of the first electric motor and/or the second internal rotor of the second electric motor are comprised by the shaft.

While an open impeller is generally less efficient than a closed impeller, the open impeller is better suited for pumping blood comprising clots as it provides fewer adhesion points to which blood might attach, potentially leading to a build-up of clots and the danger of pump clogging. The open impeller is structurally and fluidically less complex than the closed impeller.

The merging portion of the open impeller particularly consists of the blades channels.

According to another embodiment of the invention, the first internal rotor of the first electric motor is arranged on a first portion of the shaft that is located in a first half space extending from a plane extending orthogonally to an axis of rotation of the impeller comprising the first inlet channel and wherein the second internal rotor of the second electric motor is arranged on a second portion of the shaft that is located in a second particularly complementary half space extending from said plane, such that the second half space comprises the second inlet channel.

According to this embodiment inflowing venous blood can be used for cooling the first and second electric motor, while the amount of dissipated heat is approximately equally distributed to the first and the second inlet channel which ensures that the blood temperature does not exceed a critical temperature as compared to a single motor design.

According to another embodiment a gap between the shaft and the first and/or second stator is larger than one millimeter, wherein the blood flows through the gap when pumped by the pump.

This comparably large gap reduces the motor efficiency but reduces the pressure losses before merging of the two inlets and allows for clots comprised in the blood being pumped without the risk of pump clogging. Furthermore, according to another embodiment of the invention, the gap between the first and/or the second rotor, and particularly all rotating pump components, and the first and/or the second stator and particularly an inner wall of the pump housing is larger than 1 mm.

According to another embodiment of the invention, the first and the second inlet channel are arranged opposite from each other particularly along the axis of rotation of the impeller and wherein the blades are configured such that a straight-line fluidic passage is provided and sustained between the first inlet channel and the second inlet channel through the blade channels of the impeller and/or through the eyes of the impeller, such that a pressure difference between the first and the second blood flow is reduced or ideally equalized before the first and the second blood flow are pumped to the first outlet channel.

The pump comprises a straight-line fluidic passage particularly when in a cross-sectional view along the axis of rotation a straight line can be drawn between the first inlet channel and the second inlet channel, without the line being obstructed by a component of the pump, particularly the impeller.

The straight-line passage can for example extend through the blade channels of an impeller or through the eyes of a closed impeller.

such a straight-line passage allows for a merging of flows prior to or simultaneous with pumping the blood flows from the first and second inlet channel towards the outlet channel.

Furthermore, the pump is less susceptible for clogging due to clots in the blood.

In case the impeller is an open impeller, the straight-line passage is for example located along the gap between the first and/or second rotor and an inner wall of the pump housing.

In case the impeller is a double-suction closed impeller, the straight-line passage extends through the eyes of the impeller, i.e. blood could flow along a straight line from the first inlet channel to the second inlet channel if the pump is not working properly, even though this is not a desired situation.

It is noted that, when the first and/or second rotor rotate, said straight-line passage particularly rotates as well around the axis of rotation of the impeller.

The straight-line fluidic passage is particularly of cylindrical shape.

The straight-line fluidic passage extends particularly parallel to the axis of rotation if the impeller.

According to another embodiment of the invention, the radial blood pump has a housing comprising the first and/or second stator, the housing encasing at least the following components:
  a) the impeller;
  b) the first and/or the second internal rotor;
  wherein a distance between an inner wall portion of the housing and said components is at least 0.25 mm particularly at least 0.5 mm throughout the blood pump such that an appropriate washout to prevent thrombus formation is facilitated, venous blood clots cannot clog the blood pump and the heat losses generated by the motor are sufficiently removed.

According to another embodiment of the invention, the blood pump comprises an active magnetic bearing, particularly a bearingless first and/or second motor, or wherein the blood pump comprises a mechanical bearing particularly arranged at an entry of the first and/or second inlet channel such that venous blood can be used for cooling the bearing.

The magnetic bearing particularly comprises magnets and control coils as well as sensors for estimating/measuring a position of the rotor at least along one direction. The bearing position is adjusted according to the sensor data.

A magnetic bearing has the advantage that it is contactless and no frictional heat is generated at the bearings. This comes at the cost of increased space requirement of the pump.

Alternatively, the blood pump can comprise mechanical bearings. While frictional heat is produced by rotating mechanical bearings and while mechanical bearings suffer from wear and tear, the space requirements are smaller and no additional electric power is needed for components of the mechanical bearing. Mechanical bearing in blood pumps indicate acceptable wear [9] and a well-washed design without disturbed flow fields even in off-design conditions will minimize the risk of heat and thrombi generation: Bearing structures are located in a larger distance to impeller inlet regions so that the flow field around the bearing is much smoother than e.g. in the mechanically supported HeartMate II (Abbott Inc, Chicago, Illinois, USA).

According to another embodiment of the invention, the blood pump comprises a second outlet channel to which a blood flow from the first and/or the second inlet channel can be pumped by the impeller, particularly wherein the second outlet channel is arranged in a tangential direction with respect to the impeller, particularly along the radial impeller plane, particularly wherein the second outlet channel points in an opposite direction as the first outlet channel.

All embodiments regarding the first outlet channel and all advantages associated with the pump with regard to the first outlet channel apply in a similar manner to the second outlet channel.

The second outlet channel particularly has the same dimensions and the same shape as the first outlet channel.

This embodiment allows the distribution of blood flows in two blood vessels and reduces the radial force on the impeller and therefore on the bearings.

The first and second outlet channel are particularly connected to the left and right pulmonary arteries.

The problem according to the invention is furthermore solved by a system with a blood pump according to the invention, and a device for electric power transfer, such as wire-bound or an inductive transcutaneous power transfer, wherein the system further comprises a sensor for measuring and/or estimating a hemodynamic signal and a controller that is configured to adjust a pump rate of the blood pump according to the hemodynamic signal, wherein the sensor is particularly a pressure sensor arranged at the blood pump or wherein the sensor can be arranged in the cardiovascular system suitable to measure and/or estimate a blood pressure in a vessel or a pressure difference between two cavities or the pressure difference across the pump between at least one inlet and one outlet.

The system allows for adjusting the blood pump rate based on the determined pressure particularly the pressure difference. Such a system allows responding to the varying need of cardiac output and therefore oxygen consumption of a patient. For example, when the patient sleeps, less cardiac output is required as compared to when the patient is physically active and the body requires a higher cardiac output. The system adjusts the blood flow rate accordingly by keeping the pressure in the IVC/SVC or the pressure difference across the pump or between the IVC and the systemic atrium constant or in a predefined range.

In order to adjust the pump rate, the sensor measures particularly a blood pressure in the blood vessel, which can serve as an indicator for the actual cardiac output demand of the body.

However, also other hemodynamic signals can be sensed by a pressure sensor and used for adjusting the pump rate, such as for example a heart frequency or the pump flow.

Typically, the blood pump needs to have an external power supply in the vicinity of the body of the patient. In case the system is a wire-bound system, the power is transmitted from the power supply via the device for electric power transfer to the blood pump by means of a cable via a percutaneous access, rendering the system less handy and prone to inflammatory diseases at the percutaneous access.

The power supply is for example for a wearable battery pack. The system particularly also comprises the wearable power supply.

Due to the low power requirements for a radial blood pump in the cavopulmonary position, the system can be fully implantable, particularly with transcutaneous energy transfer comprising implantable batteries.

The problem according to the invention is furthermore solved by a system with a blood pump according to the invention, and a device for electric power transfer, such as wire-bound or inductive transcutaneous power transfer According to another embodiment of the invention, the device for electric power transfer is configured to wirelessly transfer the electric power to the blood pump, wherein the electric power transfer device comprises a power receiver and a power transceiver, wherein the power receiver is electrically connected to the blood pump in the patient's body and configured for providing the blood pump with electric energy transferred from the electric transceiver to the electric receiver, wherein the electric transceiver is particularly located outside the patient's body.

A wireless power transfer omits a percutaneous access and thus the risk of inflammation is reduced and a higher flexibility in terms of handiness of the system is achieved.

Moreover, the controller of the system for adjusting the pump rate can be arranged outside the patient's body as well, reducing the need for extra power delivered into the patient's body.

The problem according to the invention is furthermore solved by a method for adjusting a blood pump rate according to a hemodynamic signal with a system according to the invention, comprising the steps of:

Assessing, particularly measuring a hemodynamic signal of a patient having implanted the radial blood pump, particularly wherein the hemodynamic signal is at least an inlet channel pressure at the first and/or second inlet channel and/or at least one outlet channel pressure at the first and/or second outlet channel, or wherein the hemodynamic signal is a pressure difference between the atrium and the inferior vena cava of the heart or wherein the hemodynamic signal is a pressure difference between at least one of the inlet channels, i.e. the first and/or the second inlet channel, and one of the outlet channels, i.e. the first and/or the second outlet channel;

Determining from the hemodynamic signal a required pump output rate of the blood flow for the first and/or second output channel particularly of the venous blood flow entering through the first and second inlet channel;

Adjusting the blood pump, particularly the pump speed of the blood pump, such that the determined pump output rate is achieved particularly such that the hemodynamic signal is kept within a predefined range The blood pump is particularly adjusted such that the at least one inlet channel pressure (for example at the first and/or second inlet channel) or the pressure difference between the atrium and the inferior vena cava of the heart or the pressure difference between at least one of the inlet channels, i.e. the first and/or the second inlet channel, and one of the outlet channels, i.e. the first and/or the second outlet channel are kept within a predefined range.

The pump output rate is particularly a blood flow, particularly in terms of a blood volume pumped per time unit.

According to another embodiment of the method, a differential pressure of the cardiovascular system is estimated from a hemodynamic signal sensed by a differential pressure sensor of the system.

According to another embodiment of the invention, the system further comprises a processing unit for processing sensor data of the system.

According to another embodiment of the method, the processing unit provides a mean differential pressure signal.

According to another embodiment of the invention, the controller of the system receives a controller signal, wherein the controller signal comprises information on the deviation of a target pressure, particularly a target pressure difference, and an estimated pressure, particularly an estimated pressure difference.

According to another embodiment of the invention, the radial blood pump is a pump to support the Fontan circulation at the cavopulmonary junction, particularly a Fontan pump.

According to another embodiment of the invention, the radial blood pump provides particularly beneficial fluid dynamic properties over a wide range of operating conditions that are achieved by a well-guided flow and avoidance of any stagnation and recirculation regions in within the pump.

According to another embodiment of the invention, the radial blood pump comprises a ring chamber particularly instead of a real volute casing.

This allows a wide operating range of the pump. Particularly shear stresses are lower than in common rotary blood pumps promising a low blood trauma profile. Hydraulic properties of the pump indicate pressure sensitive characteristics (typical slope of −2−5 mmHg/(L/min). Such a flat pressure-flow relationship (HQ curve) ensures intrinsic adaptation of the pump output to changes in venous return [10], particularly if no automated speed adaptation by a physiologic control algorithm is foreseen.

Figure 2:
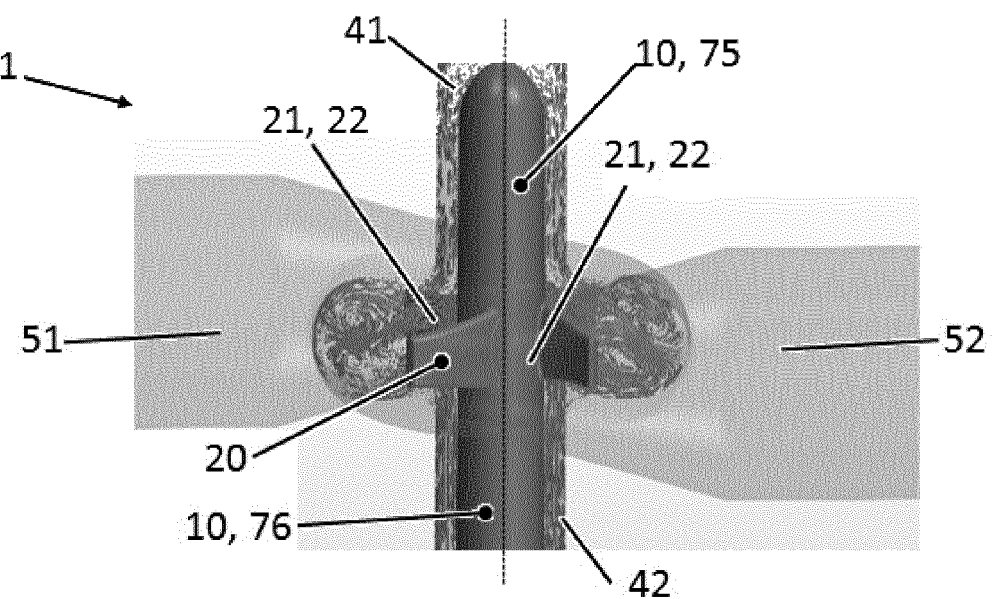
Figure 3:
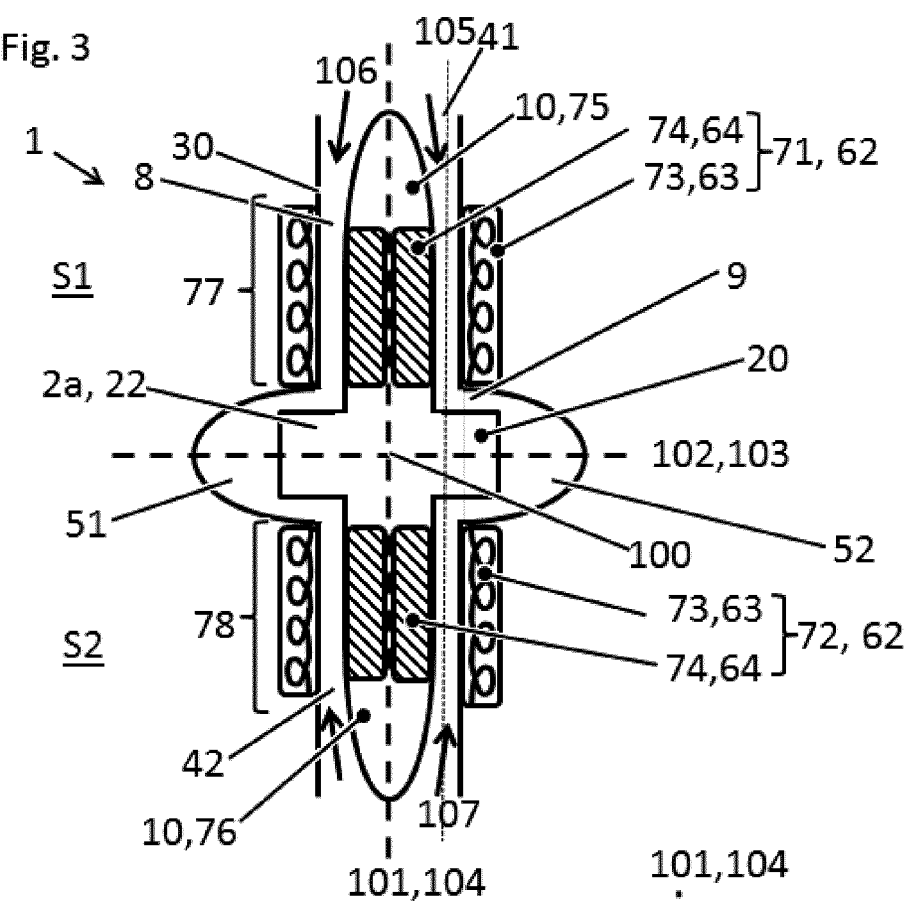
Figure 4:
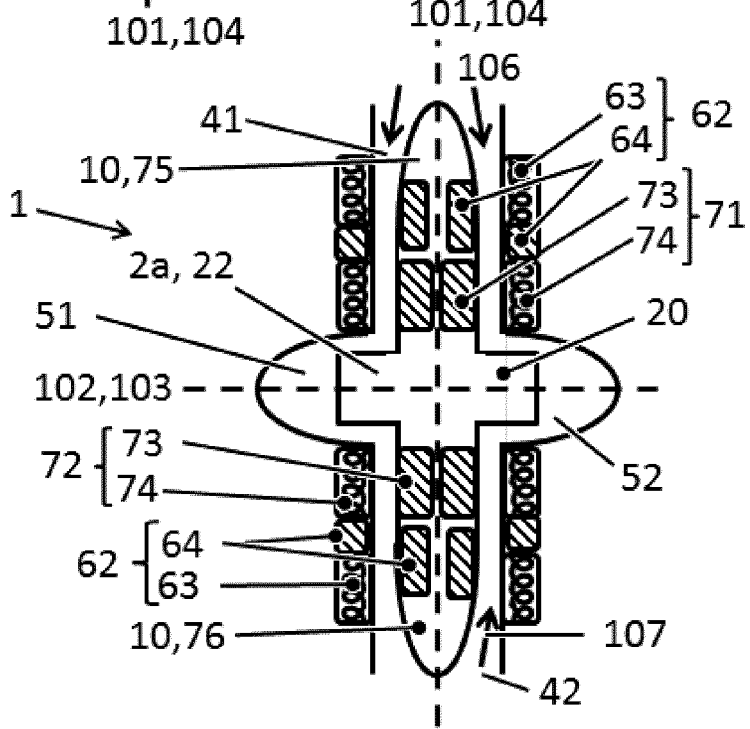
Figure 5:
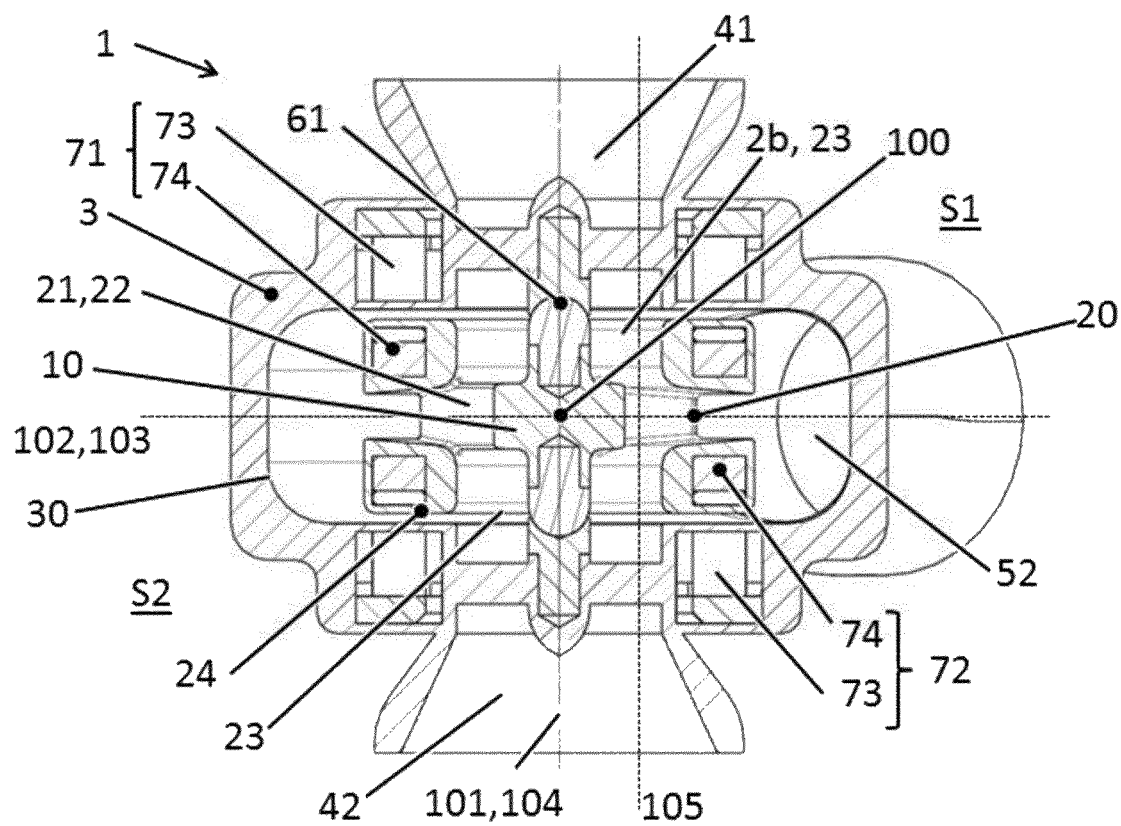
Figure 6:
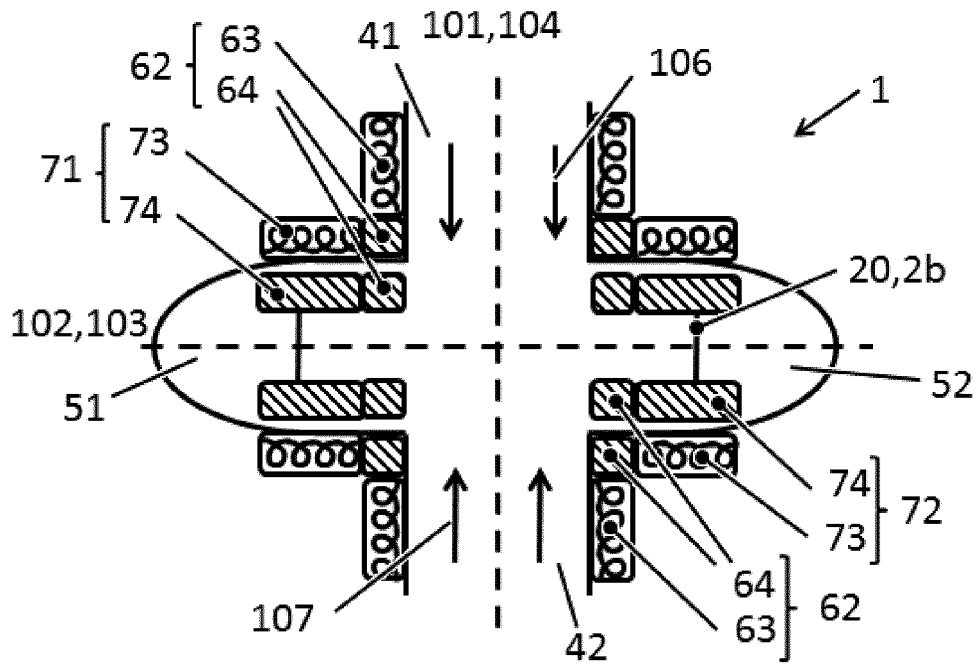
Figure 7:
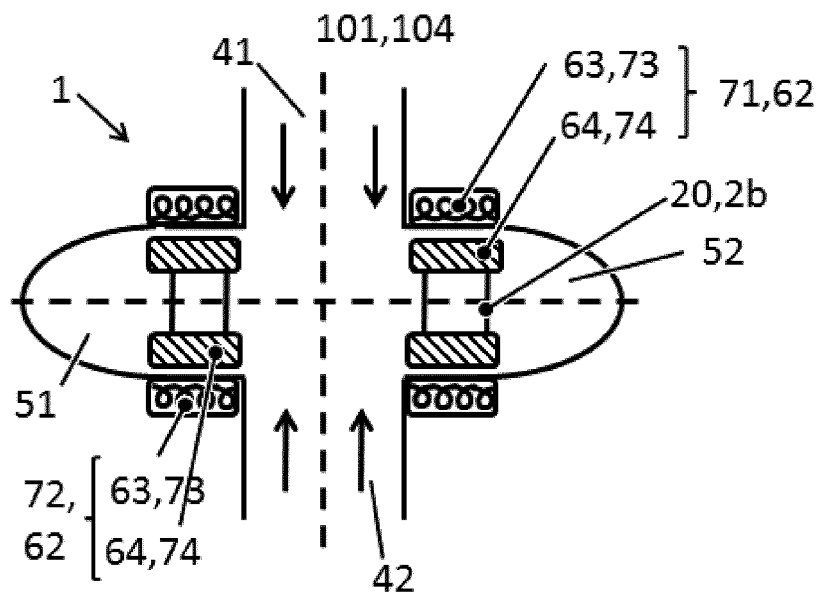
Figure 8:
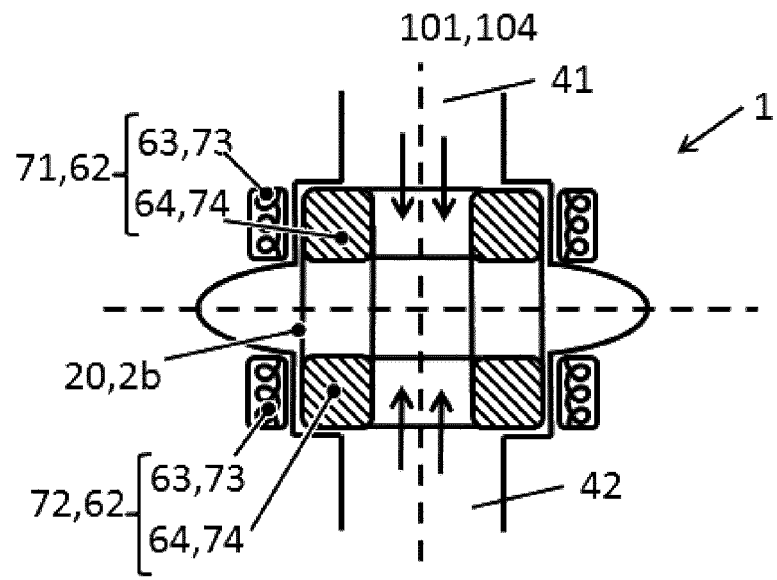
Figure 9:
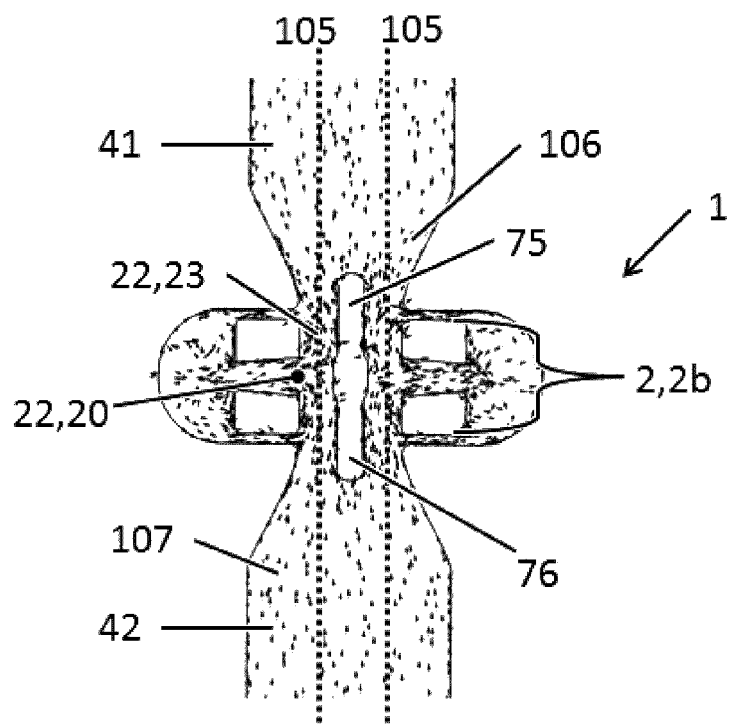
Figure 10:
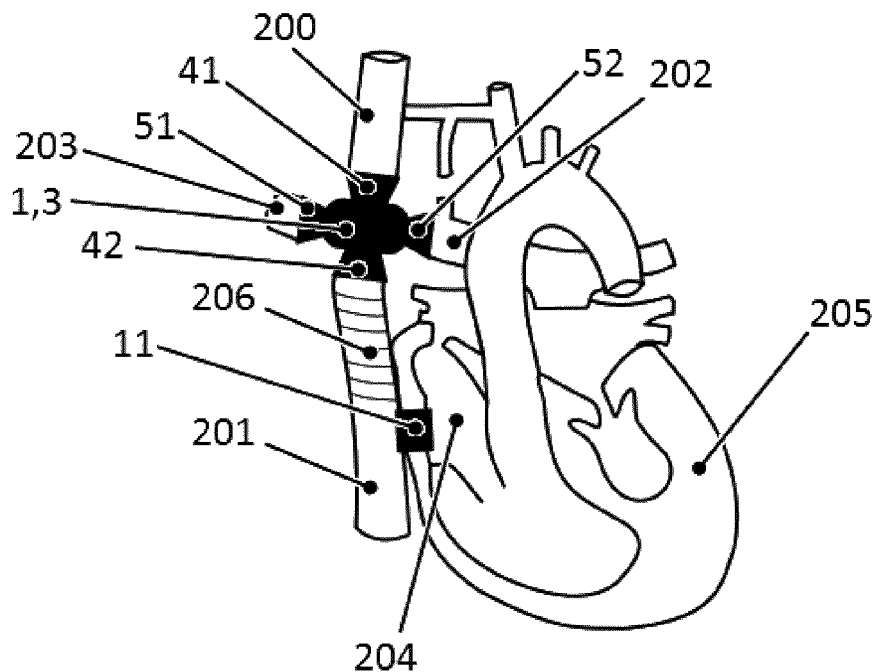
Figure 11:
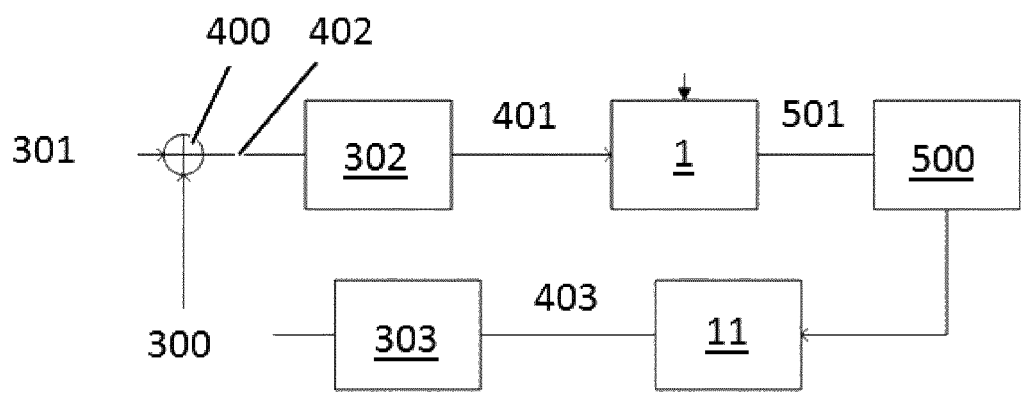

In the following, the invention is explained in detail with reference to exemplary embodiments shown in the figures. It is noted that the drawings are not necessary to scale. It is shown in FIG. 1 a cross-sectional view of a radial blood pump according to the invention with an open impeller and mechanical bearings;

FIG. 2 a perspective view of a radial blood pump according to the invention with an open impeller and mechanical bearings:

FIG. 3 a cross-sectional view of a radial blood pump according to the invention with an open impeller and merged magnetic bearings:

FIG. 4 a cross-sectional view of a radial blood pump according to the invention with an open impeller and separate magnetic bearings:

FIG. 5 a cross-sectional view of a radial blood pump according to the invention with a closed impeller and mechanical bearings:

FIG. 6 a cross-sectional view of a radial blood pump according to the invention with a closed impeller and separate magnetic bearings:

FIG. 7 a cross-sectional view of a radial blood pump according to the invention with a closed impeller and merged magnetic bearings:

FIG. 8 a cross-sectional view of a radial blood pump according to the invention with a closed impeller and separate magnetic bearings:

FIG. 9 a flow profile through a radial blood pump according to the invention with a closed impeller;

FIG. 10 a system according to the invention with a blood pump and a pressure sensor; and FIG. 11 a schematic flow diagram of a method for controlling with the system according to the invention.

FIG. 1 to FIG. 9 show various views and embodiments of the radial blood pump 1. In all depicted embodiments the blood pump 1 is designed symmetrically with respect to a central point 100 where the vertical axis 101 and the horizontal axis 102 intersect, or to a radial plane 103 extending orthogonally to the vertical line 101 and comprising the horizontal line 102. The vertical line 101 corresponds to the axis of rotation 104 of a single impeller 2 that is arranged in the housing 3 of the blood pump 1.

The symmetric pump design, particularly the oppositely arranged inlet channels 41, 42 and outlet channels 51, 52, reduces hydraulic forces on the impeller 2 and thus the bearings 60.

The radial plane 103 divides the space in a first half space S1 comprising the first inlet channel 41 of the pump 1 and a second half space S2 comprising a second inlet channel 42 of the pump 1.

The first and the second inlet channel 41, 42 are arranged opposite of each other and form a straight tube.

When the radial blood pump 1 is implanted in a patient, the first inlet channel 41 is connected to the superior vena cava 200, while the second inlet channel is connected to the inferior vena cava 201.

The blood flow 200 entering the radial blood pump 1 is depicted as arrows.

The impeller 2 of the radial blood pump 1 rotates around the axis of rotation 104 and is centered on the central point 100. In the embodiments shown, the pump 1 always comprises two outlet channels 51, 52 that are arranged on opposite sides pointing in a radial direction of the radial blood pump 1.

The first and second outlet channel 51, 52 extent tangentially with respect to the impeller 2.

The impeller 2 is driven by a first and a second electric motor 71, 72, wherein in the depicted embodiments the first electric motor 71 is arranged in the first half space S1, while the second electric motor 72 is arranged in the second half space S2.

The impeller 2 is designed as a double-suction impeller 2 comprises a plurality of blades 20 that form blade channels 21 through which the blood is pumped towards at least one outlet channel 51, 52.

The first and the second electric motor 71, 72 comprise motor coils 73 and motor magnets 74 and are brushless DC motors, facilitating a contactless actuation and requiring less maintenance.

The motor coils 73 are arranged in the housing 3 of the pump 1 and can be connected to a power supply and a controller controlling the motor speed (not shown). The housing 3 therefore comprises or can be considered the first and second stator of the first and the second electric motor 71, 72 respectively.

The motor magnets 74 of the first and the second motor 71, 72 are arranged on a first and second rotor 75, 76 of the first and second motor 71, 72 respectively.

The first and the second rotor 75, 76 are rigidly connected or coupled to each other such that the first and the second motor 71, 72 always turn at the same speed.

The presence of two independently driven but synchronized electric motors 71, 72 with rigidly connected rotors 75, 76 provides a failsafe option to the radial blood pump 1, in case one motor is damaged or otherwise compromised such that it could not maintain a desired pump speed. In case one motor fails the other motor is capable to maintain a desired pump speed or at least an emergency pump speed that is safe for the patient.

In general, all embodiments of the pump 1 have comparably large fluid channels 8 and gaps 9 for the blood flow and thus provide a comparably low resistance against floating thrombi.

Moreover, the blood pump 1 is designed such that recirculation and stagnation of blood in the pump 1 is avoided. This is for example achieved by opposite inlet and outlet channels 41, 42, 51, 52, well designed flow paths and large gaps 9.

An ideal hepatic flow distribution is achieved as the pump 1 is designed to discharge the well-mixed blood entering through the first and the second inlet channel 41, 42 to opposite outlet channels 51, 52, preventing degeneration of pulmonary vasculature.

In FIG. 1 and FIG. 2 an embodiment of the radial pump 1 is shown that comprises an open impeller 2a. The radial blood pump 1 comprises a shaft 10 that extends along the axis of rotation 104 of the impeller 2a. The impeller 2a together with the blades 20 is integrally formed to the shaft 10. The shaft 10 comprises the motor magnets 74 of the first and second motor 71, 72. Thus, the shaft 10 comprises the impeller 2a and the first and second rotor 75, 76.

Between all rotating components, i.e. the shaft 10 with all its components and an inner housing wall 30 of the radial blood pump 1, a gap size of at least 1 mm is sustained, such that even clots of blood can be pumped by the pump 1. The dimension of the gap 9 also prevents adhesion and formation of blood clots in the pump 1.

The first and the second motor 71, 72 are cooled by blood flowing through the respective inlet channel 41, 42. The heat dissipated by the motors 71, 72 leads to an increased temperature of the blood. As clot formation depends inter alia on the blood temperature it is advantageous to arrange the first and second motor 71, 72 along different inlet channels 51, 52 in order to avoid a temperature increase beyond a critical clot-formation temperature.

The shaft 10 of the radial blood pump 1 comprises mechanical bearings 61 at its axial ends. The mechanical bearings 61 can be ball cup bearings consisting of ceramics such as ruby.

Mechanical bearings 61 are resistant against axial forces and also allow small pump sizes. However, a mechanical bearing 61 generates additional heat and disturbed flow fields which can both lead to blood trauma and clot formation. Materials with excellent tribological properties as well as a high thermal conductivity limit wear to an acceptable extent, thereby minimizing this risk which is further reduced by a well-washed design. Moreover, the mechanical bearings 61 are located in a comparably large distance to the impeller merging portions 22, here the blade channels 21, so that the flow field around the mechanical bearings 61 is much smoother than e.g. in the mechanically supported HeartMate II (Abbott Inc, Chicago, Illinois, USA).

In FIG. 3 a cross-section of an embodiment similar to FIG. 1 and FIG. 2 is shown. However, in contrast to the radial blood pump 1 in FIG. 1 and FIG. 2, the radial blood pump 1 does not comprise mechanical bearings 61, but magnetic bearings 62, keeping the shaft 10 on the central axis 101. Each stator 77, 78 comprises bearing coils 63 and bearing sensors (not shown) that are placed around the axial flow path. Radial position control of the shaft 10 (and thus the first and second rotor 75, 76) is performed using the bearing coils 63 and bearing sensors. Axial positioning of the shaft 10 is achieved by reluctance forces.

The motor coils 73 and bearing coils 63 are be integrated into one functional unit in this example, of an essentially bearingless motor. The magnetic bearings 62 work contactless and show no mechanical wear.

FIG. 4 shows a similar design as depicted in FIG. 3, however, with magnetic bearing coils 63 and bearing magnets 64 separate and distinct from the motor coils 73. In this embodiment the radial levitation is achieved passive magnetically (repelling magnets 64). The control coil(s) 63 control the rotors position in a way the axial magnetic forces of the repelling bearing magnets acting on the impeller always equalize the axial thrust forces and the rotor is levitated with a minimum power demand. (Zero force control). The reference sings in all figures refer to functional similar or identical means and are therefore not re-iterated for each figure.

FIG. 5 to FIG. 9 show radial blood pumps 1 with a closed impeller 2b design. Reference signs from previous figures apply as long as not explicitly mentioned otherwise. Function and specific arrangement of the pump components have been explained above and apply similarly to the closed-impeller designs 2a as long as not indicated otherwise.

In FIG. 5 a radial blood pump 1 with mechanical bearings 61 is shown.

FIG. 5 shows a cross-sectional view of the pump 1.

The impeller 2 is a double-suction closed impeller 2b, wherein the merging portion 22 of the impeller 2b is located in the eyes 23 of the impeller 2b as well as in the blade channels 21. A straight-line flow connection 105 between the first and second inlet channel 41, 42 is located centrally around the axis of rotation 104.

In the embodiment the first motor 71 is arranged in the first half space S1 and the second motor 72 is arranged in the second half space S2. The motor coils 73 are arranged on the respective first and second stator 77, 78 formed by the housing 3 of the pump 1. The closed impeller 2b has two shrouds 24 covering the blades 20. Blood from the first and second inlet channel 41, 42 flows through the eyes 23 of the impeller 2b and mix at the central region of the impeller 2b, the merging portion 22.

Motor magnets 74, 75 are comprised by the impeller 2b, particularly by the shrouds 24 of the impeller 2b.

In contrast to an open impeller the closed impeller 2b is more efficient and allows for almost equal flow around the upper and lower motor region in the secondary flow path even in case of imbalanced inflow/outflow situations. Further, the shroud 24 is beneficial in terms of blood damage compared to an open impeller.

FIG. 6 shows a schematic cross-section of a radial blood pump 1 with a closed impeller 2b and magnetic bearings 62.

The magnetic bearings 62 comprise bearing magnets 64, bearing coils 63 and bearing sensors (not shown). In this embodiment the radial levitation is achieved passive magnetically (attractive magnets). The control coil(s) control the rotors position in a way the axial magnetic forces of the attracting bearing magnets acting on the impeller always equalize the axial thrust forces and the the rotor is levitated with a minimum power demand. (Zero force control). The motor magnets 74 of the first and second motor 71, 72 as well as the bearing magnets 64 are placed within the shrouds 24 of the impeller 2b. Axial position control is achieved using the bearing coils 63 and bearing sensors (not shown). Radial positioning is achieved passively.

FIG. 7 shows an embodiments with magnetic bearings 62 merged with the electric motors 71,72 (axial bearingless motor), wherein the bearings 62 (and thus the motors 71, 72) are arranged such that the axial position of the impeller 2b is actively controllable, while the radial position of the impeller 2b is achieved passively (reluctance forces). The motor magnets 74 and the bearing magnets 64 are merged and formed as a single magnet each.

FIG. 8 shows an embodiment with magnetic bearings 62 merged with the electric motors 71,72 (axial bearingless motor), wherein the bearings 62 (and thus the motors 71, 72) are arranged such that the radial position of the impeller 2b is actively controllable, while the axial position of the impeller 2b is achieved passively (reluctance forces). The motor magnets 74 and the bearing magnets 64 are merged and formed as a single magnet each.

In FIG. 9 the flow profile of a blood flow through the operating radial blood pump 1 is shown. The depicted radial blood pump 1 is a blood pump with a closed impeller 2b.

The bearings are not shown in this embodiment.

The arrows indicate the flow velocity in the pump 1 at the location of the arrow.

As can be seen, the merging portion 22 in the closed impeller 2b embodiments is in the central region of the impeller 2b at the eyes 23 and at the blade channels 20 of the closed impeller 2b.

Thus, the merging of the blood flows from the first and second inlet channel 41, 42 takes place before and simultaneously with the blood being transported towards the outlet channels 51, 52. This allows for a pressure equalization between the two inlet channels 41, 42 such that symmetric forces are sustained within the pump 1. Many straight-line connections 105 between the first inlet channel 41 and the second inlet channel 42 exist and are exemplary indicated with dotted lines. The straight-line connections 105 allow for an instant pressure equalization between the inlet channels 41, 42.

FIG. 10 shows a part of the system according to the invention. The radial blood pump 1 is connected to the respective blood vessels 200, 201, 202, 203 of the heart 205 and support the Fontan circulation of the heart 205. With the first inlet channel 41 the pump 1 is connected to the SVC 200, with the second inlet channel the pump is connected to the IVC 201 via a graft 206, with the first outlet channel 51 the pump 1 connected to the left pulmonary artery 202 and with the second outlet channel 52, the pump is connected to the right pulmonary artery 203

Additionally, a differential pressure sensor 11 is arranged between the atrium of the heart 205 and one of the inlet channels 41, 42, here the second inlet channel 42 of the radial blood pump 1.

The data from the pressure sensor 11 is then used for adjusting the pump rate of the pump 1.

This is shown in FIG. 11. The estimated differential pressure 300 is compared 400 to a desired differential pressure 301. A signal coding the deviation 402 between the desired and estimated differential pressure 300, 301 is provided to a controller 302 of the system. The controller 302 adjusts 401 the pump speed accordingly such that the deviation 402 between the desired pressure 301 and estimated pressure 300 is minimized. The pressure sensor data 403 are processed prior to the comparison with a processor 303 in order to provide an appropriate response. This way the blood flow 200 in the cardiovascular system 500 can be controlled in a robust and fail-safe manner.

The invention provides a blood pump 1, particularly a Fontan pump with reduced space requirements and robust and fail-safe operation.

REFERENCES

[1] M. Gewillig, "The fontan circulation," Heart, vol. 91, pp. 839-846, 2005.

[2] D. J. Goldberg, R. E. Shaddy, C. Rivashankar, and J. Rychik, "The failing Fontan: etiology, diagnosis and management," Expert Rev. Cardiovasc. Ther., vol. 9, no. 6, pp. 785-793, 2011.

[3] K. N. Pundi, J. N. Johnson, J. A. Dearani, K. N. Pundi, Z. Li, C. A. Hinck, S. H. Dahl, B. C. Cannon, P. W. O'Leary, D. J. Driscoll, and F. Cetta, "40-Year Follow-Up after the Fontan Operation Long-Term Outcomes of 1,052 Patients," *J. Am. Coll. Cardiol.*, vol. 66, no. 15, pp. 1700-1710, 2015.

[4] Y. d'Udekem, A. J. Iyengar, J. C. Galati, V. Forsdick, R. G. Weintraub, G. R. Wheaton, A. Bullock, R. N. Justo, L. E. Grigg, G. F. Sholler, S. Hope, D. J. Radford, T. L. Gentles, D. S. Celermajer, and D. S. Winlaw, "Redefining Expectations of Long-Term Survival After the Fontan Procedure: Twenty-Five Years of Follow-Up From the Entire Population of Australia and New Zealand," *Circulation*, vol. 130, no. 11_suppl_1, pp. S32-S38, 2014.

[5] M. D. Rodefeld, B. Coats, T. Fisher, G. A. Giridharan, J. Chen, J. W. Brown, and S. H. Frankel, "Cavopulmonary assist for the univentricular Fontan circulation: Von Kármán viscous impeller pump," *J. Thorac. Cardiovasc. Surg.*, vol. 140, no. 3, pp. 529-535, 2010.

[6] C. M. Haggerty, F. Fynn-Thompson, D. B. McElhinney, A. M. Valente, N. Saikrishnan, P. J. Del Nido, and A. P. Yoganathan, "Experimental and numeric investigation of Impella pumps as cavopulmonary assistance for a failing Fontan," *J. Thorac. Cardiovasc. Surg.*, vol. 144, no. 3, pp. 563-569, 2012.

[7] R. Prêtre, A. Häussler, D. Bettex, and M. Genoni, "Right-Sided Univentricular Cardiac Assistance in a Failing Fontan Circulation," *Ann. Thorac. Surg.*, vol. 86, no. 3, pp. 1018-1020, 2008.

[8] M. R. Mehra, Y. Naka, N. Uriel, D. J. Goldstein, J. C. Cleveland, P. C. Colombo, M. N. Walsh, C. A. Milano, C. B. Patel, U. P. Jorde, F. D. Pagani, K. D. Aaronson, D. A. Dean, K. McCants, A. Itoh, G. A. Ewald, D. Horstmanshof, J. W. Long, and C. Salerno, "A Fully Magnetically Levitated Circulatory Pump for Advanced Heart Failure," *N. Engl. J. Med.*, vol. 376, no. 5, pp. 440-450, 2017.

[9] K. S. Sundareswaran, S. H. Reichenbach, K. B. Masterson, K. C. Butler, and D. J. Farrar, "Low Bearing Wear in Explanted HeartMate II Left Ventricular Assist Devices After Chronic Clinical Support," *ASAIO J.*, vol. 59, no. 1, pp. 41-45, 2013.

[10] M. Granegger, M. Schweiger, M. Schmid Daners, M. Meboldt, and M. Hübler, "Cavopulmonary mechanical circulatory support in Fontan patients and the need for physiologic control: A computational study with a closed-loop exercise model," *Int. J. Artif. Organs*, March 2018.

The invention claimed is:

1. A radial blood pump (1), for supporting a blood flow (106) in a human or animal heart (205) comprising at least the following components:

A first and a second inlet channel (41, 42),

A first outlet channel (51, 52),

A first electric motor (71) comprising a first stator (77) and a first internal rotor (75), wherein the first electric motor (71) is configured to drive An impeller (2, 2*b*) arranged at an intersection of the first with the second inlet channel (41, 42), wherein the impeller (2, 2*b*) is connected to the first internal rotor (75) and wherein the impeller (2, 2*b*) comprises a merging portion (22) arranged at the intersection, where a merging of a first blood flow (106) coming from the first inlet channel (41) and a second blood flow (107) coming from the second inlet channel (42) takes place, wherein the impeller (2, 2*b*) is configured to pump the first and second blood flow (106, 107) from the first and second inlet channel (41, 42) via the merging portion (22) to the first outlet channel (51), A plurality of blades (20) comprised by the impeller (2, 2*b*), wherein the blades (20) form blade channels (21) comprised by the merging portion (22), wherein each blade (20) is arranged and configured to pump the first and second blood (106, 107) flow entering through the first and the second inlet channel (41, 42) towards the outlet channel (51), wherein the blood pump (1) is arranged and configured such that the first blood flow (106) and the second blood flow (107) meet at the merging portion (22), such that a pressure difference between the first and second blood flow (106, 107) is reduced before blood from first and second blood flow (106, 107) is pumped to the first outlet channel (51), wherein the impeller (2*b*) is a closed double-suction impeller, wherein the impeller (2, 2*b*) comprises a first and a second shroud (24) at least partially covering the blades (20), and wherein the merging portion (22) comprises two eyes (23), wherein the radial blood pump (1) comprises a straight line fluidic passage between the first and the second inlet channel (41, 42), wherein the straight line fluidic passage extends through the eyes (23) of the closed double suction impeller (2, 2*b*).

2. Radial blood pump according to claim 1, wherein the blood pump (1) comprises a second electric motor (72) comprising a second stator (78) and a second internal rotor (76), wherein the second internal rotor (76) is rigidly connected to the first internal rotor (75).

3. Radial blood pump according to claim 2, wherein the first electric motor (71) is arranged in a first half space (S1) extending from a plane (103) extending orthogonally from an axis of rotation (104) of the impeller (2, 2*b*) comprising the first inlet channel (41) and the second electric motor (72) is arranged in a second half space (S2) extending from the said plane (103) comprising the second inlet channel (42).

4. Radial blood pump according to claim 2, wherein the radial blood pump (1) has a housing (3) comprising the first and/or the second stator (77, 78), the housing (3) encasing at least the following components:

the impeller (2, 2*b*);
the first and/or the second internal rotor (75, 76);
wherein a distance (8, 9) between an inner wall portion (30) of the housing (3) and said components is at least 0.25 mm, preferably at least 0.5 mm throughout the blood pump (1).

5. The radial blood pump according to claim 2, wherein the second internal rotor (76) of the second electric motor (72) is arranged on the second shroud (24).

6. Radial blood pump according to claim 1, wherein the impeller (2, 2*b*) is a symmetric double-suction impeller (2, 2*b*).

7. Radial blood pump according to claim 1, wherein the two eyes (23) each have a diameter that is larger than 2.5 mm.

8. Radial blood pump according to claim 1, wherein the first internal rotor (75) of the first electric motor (71) is arranged on the first shroud (24).

9. Radial blood pump according to claim 1, wherein the first and the second inlet channel (41, 42) are arranged opposite to each other and wherein the blades (20) are configured such that the straight-line fluidic passage (105) is provided between the first inlet channel (41) and the second inlet channel (42) through the eyes (23) of the impeller (2, 2*b*), such that a pressure difference between the first and the second blood flow (106, 107) is reduced before the blood of the first and the second blood flow (106, 107) is pumped to the first or second outlet channel (51, 52).

10. Radial blood pump according to claim 1, wherein the blood pump (1) comprises an active magnetic bearing (62), or wherein the blood pump (1) comprises a mechanic bearing (61).

11. Radial blood pump according to claim 1, wherein the blood pump (1) comprises a second outlet channel (52) to which blood from the first and/or second inlet channel (41, 42) can be pumped by the impeller (2, 2b).

12. The radial blood pump according to claim 11, wherein the second outlet channel (52) is arranged in a tangential direction with respect to the impeller (2, 2b).

13. System with a blood pump (1) according to claim 1 and a device for electric power transfer, wherein the system further comprises a sensor (11) for estimating a hemodynamic signal (300) and a controller (300) that is configured to adjust a pump rate according to the determined hemodynamic signal (300).

14. System according to claim 13, wherein the device for electric power transfer is configured to wirelessly transfer the electric power to the blood pump (1), wherein the electric power transfer device comprises a power receiver and a power transceiver, wherein the power receiver is electrically connected to the blood pump (1) and configured for providing the blood pump (1) with electric energy transferred from the power transceiver to the power receiver.

15. Method for adjusting a pump rate according to a hemodynamic signal (300) with a system according to claim 13, comprising the steps of:
  Determining at least one hemodynamic signal (300) of a patient having implanted the radial blood pump (1);
  Determining from the determined hemodynamic signal (300) a required pump output rate for the first outlet channel (51);
  Adjusting the radial blood pump (1) such that the determined pump output rate is achieved.

16. The radial blood pump according to claim 13, wherein the sensor (11) is a pressure sensor.

* * * * *